(12) United States Patent
Pu

(10) Patent No.: US 8,525,133 B2
(45) Date of Patent: Sep. 3, 2013

(54) PARTICLE BEAM IRRADIATION SYSTEM AND PARTICLE BEAM IRRADIATION METHOD

(75) Inventor: Yuehu Pu, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 0 days.

(21) Appl. No.: 13/501,376

(22) PCT Filed: Oct. 1, 2010

(86) PCT No.: PCT/JP2010/067216
§ 371 (c)(1),
(2), (4) Date: Apr. 11, 2012

(87) PCT Pub. No.: WO2011/058833
PCT Pub. Date: May 19, 2011

(65) Prior Publication Data
US 2012/0199757 A1   Aug. 9, 2012

(30) Foreign Application Priority Data

Nov. 10, 2009 (JP) .................................. 2009-257094

(51) Int. Cl.
*G21K 5/04* (2006.01)
(52) U.S. Cl.
USPC ............. 250/492.1; 250/396 R; 250/396 ML; 250/398
(58) Field of Classification Search
USPC .................... 250/396 R, 396 ML, 492.1, 398
See application file for complete search history.

(56) References Cited

U.S. PATENT DOCUMENTS

| | | | | |
|---|---|---|---|---|
| 3,777,211 A | * | 12/1973 | Kuijpers | 315/382 |
| 6,034,377 A | * | 3/2000 | Pu | 250/492.3 |
| 6,268,610 B1 | * | 7/2001 | Pu | 250/492.3 |

(Continued)

FOREIGN PATENT DOCUMENTS

| | | |
|---|---|---|
| JP | 3-119641 A | 5/1991 |
| JP | 2008-154627 A | 7/2008 |

(Continued)

OTHER PUBLICATIONS

International Search Report (PCT/ISA/210) issued on Nov. 9, 2010, by Japanese Patent Office as the International Searching Authority for International Application No. PCT/JP2010/067216.

(Continued)

*Primary Examiner* — Robert Kim
*Assistant Examiner* — Wyatt Stoffa
(74) *Attorney, Agent, or Firm* — Buchanan Ingersoll & Rooney PC

(57) ABSTRACT

A particle beam irradiation system comprising a first deflector having the maximum deflection amount which enables to move a particle beam in one direction to the maximum width of a target and a second deflector having the maximum deflection amount is less than the maximum deflection amount of the first deflector performs a control in which the particle beam is moved by increasing at least a deflection amount of the second deflector when the particle beam is moved, and performs a deflection substitution control in which a deflection of the second deflector is substituted to a deflection of the first deflector by decreasing the deflection amount of the second deflector and changing a deflection amount of the first deflector so as to make a position of the particle beam in the target dwell when the particle beam dwells.

12 Claims, 10 Drawing Sheets

(56) References Cited

U.S. PATENT DOCUMENTS

| | | | |
|---|---|---|---|
| 8,154,001 B2* | 4/2012 | Flynn et al. | 250/505.1 |
| 2005/0029472 A1* | 2/2005 | Ueno et al. | 250/492.1 |
| 2006/0169924 A1* | 8/2006 | Purser et al. | 250/492.21 |
| 2007/0029497 A1* | 2/2007 | Retsky | 250/396 R |
| 2007/0075887 A1* | 4/2007 | Stovall et al. | 341/155 |
| 2009/0289196 A1* | 11/2009 | Hill et al. | 250/396 R |
| 2010/0187435 A1* | 7/2010 | Iseki et al. | 250/398 |
| 2011/0108737 A1* | 5/2011 | Pu et al. | 250/398 |
| 2011/0240875 A1* | 10/2011 | Iwata | 250/397 |
| 2012/0241612 A1* | 9/2012 | Harada et al. | 250/311 |

FOREIGN PATENT DOCUMENTS

| | | |
|---|---|---|
| JP | 2009-066106 A | 4/2009 |
| WO | WO 2009/035080 A1 | 3/2009 |
| WO | WO 2009035080 A1 * | 3/2009 |

OTHER PUBLICATIONS

Written Opinion (PCT/ISA/237) issued on Nov. 9, 2010, by Japanese Patent Office as the International Searching Authority for International Application No. PCT/JP2010/067216.

Japanese Office Action issued on Jan. 10, 2011.

* cited by examiner

PARTICLE BEAM IRRADIATION SYSTEM AND PARTICLE BEAM IRRADIATION METHOD

TECHNICAL FIELD

The present invention relates to a particle beam irradiation apparatus, for radiating a particle beam in accordance with the three-dimensional shape of a diseased site, which is included in a particle beam therapy system which performs therapy by radiating a charged particle beam onto a diseased site such as a tumor.

BACKGROUND ART

In a treatment method based on a particle beam, a high-energy particle beam, such as a proton beam or a carbon beam accelerated up to 70% of the light velocity, is utilized. These high-energy particle beams have the following features when irradiated into a body. Firstly, almost all of irradiated particle beams stop at a position of the depth proportional to the particle beam energy raised to the 1.7th power. Secondly, the density (referred to as a dose) of energy, which is given to the path through which an irradiated particle beam passes until it stops in a body, becomes maximum at a position where the particle beam stops. A distinctive deep dose distribution curve formed along a path through which a particle beam passes is referred to as a Bragg curve. The position where the dose value becomes maximum is referred to as a Bragg peak.

A three-dimensional particle beam irradiation system is contrived in such a way that, while it scans the Bragg peak position in accordance with the three-dimensional shape of a tumor and adjusts the peak dose at each scanning position, a predetermined three-dimensional dose distribution is formed in a tumor region, which is a target preliminarily determined by an imaging diagnosis. The scanning of the position where a particle beam stops includes scanning in transverse directions (X and Y directions) which are approximately perpendicular to the irradiation direction of a particle beam and scanning in a depth direction (Z direction) which is the irradiation direction of a particle beam. In the transverse-direction scanning, there exists a method of moving a patient with respect to a particle beam and a method of moving the position of a particle beam by use of an electromagnet or the like; in general, the method utilizing an electromagnet is adopted. Scanning in the depth direction is performed only by changing the energy of a particle beam. As the method of changing energy, there exists a method of changing the energy of a particle beam by means of an accelerator and a method of inserting an energy attenuator into a path through which a particle beam passes and changing the attenuation amount of the attenuator. The method of moving the position of a beam by use of an electromagnet (referred to also as scanning) is disclosed, for example, in Patent Document 1. As shown in FIG. 2 of Patent Document 1, in a particle beam irradiation system of a conventional particle beam therapy system, as a means for moving the position of a beam spot, a scanning magnet (referred to also as a scanning electromagnet) which deflects a particle beam to the X-Y direction, which is a direction perpendicular to the traveling direction of a beam (the Z direction) is utilized.

PRIOR ART DOCUMENT

Patent Document

Patent Document 1: Japanese Patent Application Laid-Open No. 2008-154627 (paragraph 0024 and FIG. 2)

DISCLOSURE OF THE INVENTION

Problems to be Solved by the Invention

In the particle beam irradiation system disclosed in FIG. 2 of Patent Document 1, in a case where the scanning speed of a particle beam is made high-speed, large-capacity power sources of scanning electromagnets are required in proportion to the inductances and the scanning speeds of the scanning electromagnets X and Y. Accordingly, the capacity of the power sources for the particle beam irradiation system increase in proportion to a required irradiation field size (proportional to a target size) and a required scanning speed. An objective of the present invention is to provide a particle beam irradiation system which can scan a particle beam at a high speed without using large-capacity scanning electric power sources and whole irradiation time is short, even in a case where a required irradiation field is large.

Means for Solving the Problem

A particle irradiation system according to the present invention is the system in which scanning is performed by repeating the operation of moving an incident particle beam in at least one direction and making the incident particle beam dwell so as to irradiate the particle beam onto a target, comprising a first deflector having the maximum deflection amount which enables to move the particle beam in one direction to the maximum width of a target; a second deflector having the maximum deflection amount which enables to move the particle beam in the one direction and whose maximum deflection amount is less than the maximum deflection amount of the first deflector; and a scanning control apparatus which controls the first deflector and the second deflector, wherein the scanning control apparatus performs a control in which the particle beam is moved by increasing at least a deflection amount of the second deflector when the particle beam is moved, and performs a deflection substitution control in which a deflection of the second deflector is substituted to a deflection of the first deflector by decreasing the deflection amount of the second deflector and changing a deflection amount of the first deflector so as to make a position of the particle beam in the target dwell when the particle beam dwells.

Advantage of the Invention

According to a particle beam irradiation system of the present invention, even in a case where a required irradiation field is large, the system enables a particle beam to scan at a high speed without using large-capacity power sources of scanning electromagnets so as to shorten whole irradiation time.

EMBODIMENTS FOR CARRYING OUT THE INVENTION

Embodiment 1

Figure 1:
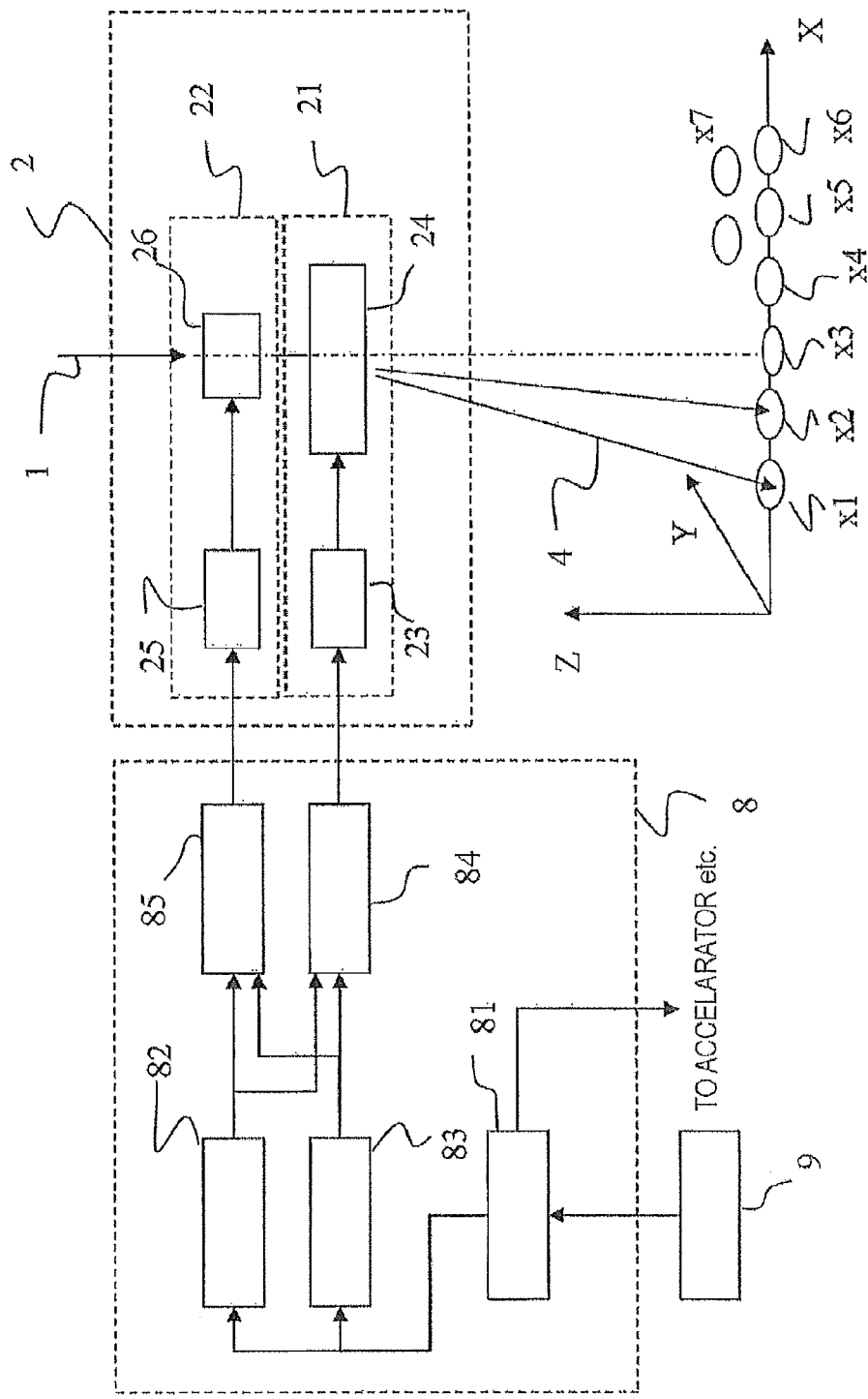
FIG. 1 is a block diagram illustrating the configuration of a particle beam irradiation system according to Embodiment 1 of the present invention.
Figure 2:
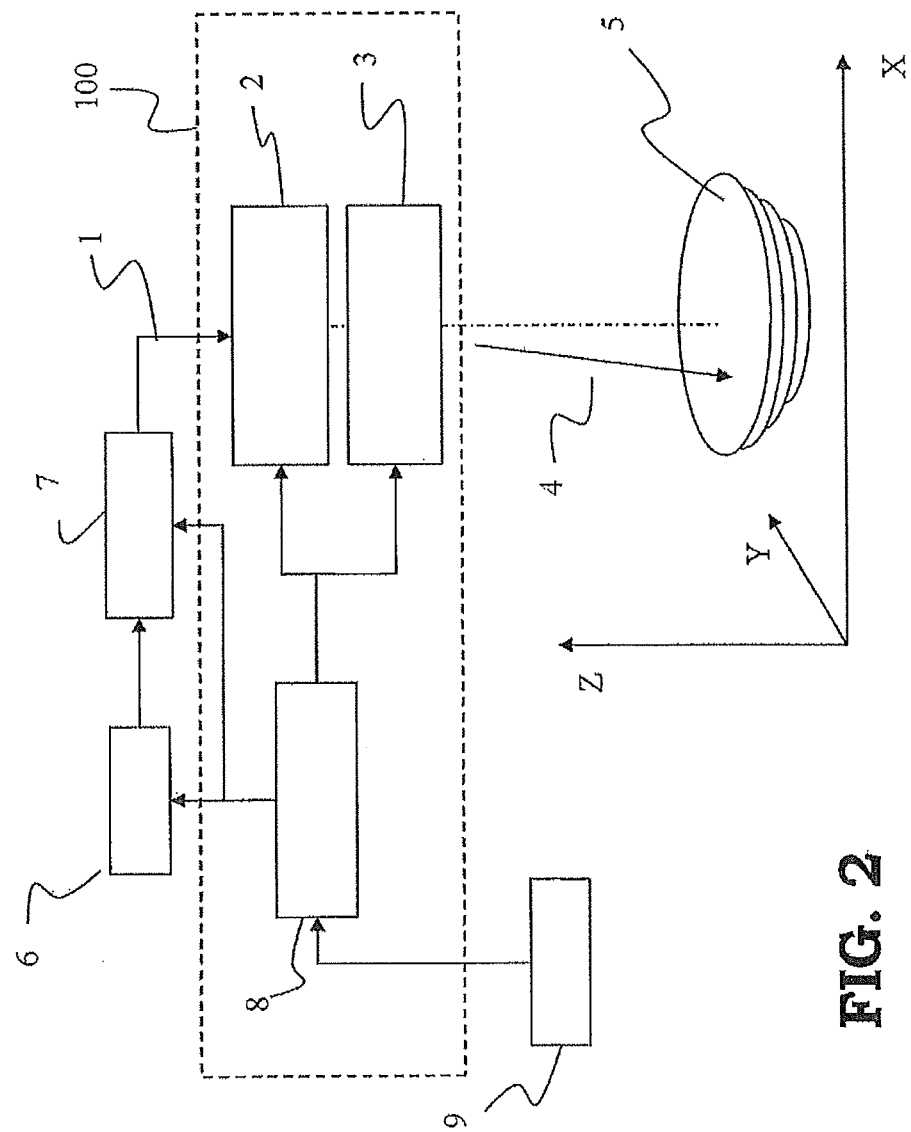
FIG. 2 is a block diagram illustrating the outline of a particle beam treatment apparatus to which the particle beam irradiation system of the present invention is applied.

FIG. 1 is a block diagram illustrating the configuration of a particle beam irradiation system according to Embodiment 1 of the present invention. FIG. 2 is a block diagram illustrating the outline of whole of particle beam therapy system to which the particle beam irradiation system of the present invention is applied. In FIG. 2, reference character 6 denotes a particle beam accelerator which generates a particle beam and accelerates the particle beam, and reference character 7 denotes a particle beam transport unit. Reference character 100 denotes a particle beam irradiation system which scans a particle beam 1 which is inputted from the particle beam transport unit 7 so as to irradiate a particle beam 4 onto a target 5. The particle beam irradiation system 100 is a subject matter of the present invention. Reference character 2 denotes an X-direction scanning apparatus which scans a particle beam in an X-direction, one of directions which is perpendicular to the traveling direction of a particle beam, so as to change a position of a particle beam in an X-direction at each step. Similarly, reference character 3 denotes a Y-direction scanning apparatus which scans a particle beam position in a Y-direction which is perpendicular to both of the traveling direction of a particle beam and an X-direction. Reference character 8 denotes a scanning control apparatus and a reference character 9 denotes a therapy planning apparatus. The therapy planning apparatus 9 calculates the data which is required by the scanning control apparatus 8 for scanning control and transmits the data to the scanning control apparatus 8.

In FIG. 2, reference character 5 denotes a target which is an irradiation subject of the particle beam 4 and is illustrated by a schematic perspective view. The particle beam transport unit 7 is formed of, for example, a group of electromagnets. The particle beam accelerator 6 includes a synchrotron accelerator, a cyclotron accelerator, or other type of accelerator such as a dielectric wall accelerator, a laser accelerator and the like.

FIG. 1 is a block diagram illustrating the configuration of the main part of the present invention, and is a diagram illustrating the outline of the X-direction scanning apparatus 2 and the scanning control apparatus 8 shown in FIG. 2. In FIG. 1, the X-direction scanning apparatus 2 has the following configuration. Reference character 21 denotes an X-direction first deflector which deflects a particle beam in an X-direction, and comprises an X-direction first deflection electromagnet 24 and an X-direction first power source 23 which drives the X-direction first deflection electromagnet 24, that is, which supplies electric current to an exciting coil of the X-direction first deflection electromagnet 24. Reference character 22 denotes an X-direction second deflector which deflects a particle beam in an X-direction which is the same direction as that of the X-direction first deflector 21, and comprises an X-direction second deflection electromagnet 26 and an X-direction first power source 25 which drives the X-direction first deflection electromagnet 26. A particle beam is irradiated onto a diseased site while a position of the particle beam on the target 5 is changed by deflecting the particle beam with the X-direction first deflector 21 and the X-direction second deflector 22. Irradiation is performed by moving a particle beam by a predetermined distance in one direction (this movement is referred as a step) and then stopping the particle beam. That is, the particle beam is made dwell there, and then the particle beam is irradiated onto a diseased site. The position where the particle beam is made dwell is called a spot position, and this irradiation method is called a spot scanning irradiation. In FIG. 1, X1, X2, . . . and X7 denote spot positions of the particle beam 4 in an X-direction on the target 5 in performing a spot scanning irradiation.

In order to realize the above-mentioned spot scanning irradiation, the scanning control apparatus 8 has the following configuration. Reference character 81 denotes a scanning control operation unit which receives the data from the therapy planning apparatus 9 and performs a necessary operation so as to scan a particle beam; reference character 82 denotes a beam position movement control operation unit which performs operation of information which is required by the X-direction first deflector 21 and the X-direction second deflector 22 so as to move a position of a particle beam; reference character 83 denotes a beam position holding control operation unit which performs operation of information which is required by the X-direction first deflector 21 and the X-direction second deflector 22 so as to make a particle beam dwell; reference character 84 denotes an X-direction first deflector control unit which receives the data from the beam position movement control operation unit 82 and the beam position holding control operation unit 83, and transmits a signal so as to control the X-direction first deflector 21; and reference character 85 denotes an X-direction second deflector control unit which receives the data from the beam position movement control operation unit 82 and the beam position holding control operation unit 83, and transmits a signal so as to control the X-direction second deflector 22.

In spot scanning irradiation, the X-direction second deflector 22 deflects the particle beam 1 which is incident is deflected so as for a position of the particle beam 4 to move between X-positions which are adjacent; at each spot. Consequently, by the X-direction second deflector 22, when the maximum range in which a particle beam can be moved on the target 5 by the X-direction second deflector 22 is designated as ΔX1 and the maximum width in an X-direction on the target is designated as XF, ΔX1 is smaller than XF. Depending on the number of steps, for example, ΔX1 is in a range of 0.1 times of XF to 0.5 times of XF. On the other hand, it is necessary for the X-direction first deflector 21 to deflect the particle beam 1 and scan a position X of the particle beam 4 on the target 5 at least in a range of XF which is a width of the target 5. That is, the maximum deflection amount (the maximum moving range of a particle beam in which a particle beam can move) which is required by the X-direction second deflector 22 is much smaller than the maximum deflection amount which is required by the X-direction first deflector 21. Consequently, it is necessary for the X-direction first deflection electromagnet 24 in the X-direction first deflector 21 to be comprised of a large electromagnet, however, the X-direction second deflection electromagnet 26 in the X-direction second deflector 22 may be comprised of a small electromagnet. In general, in order to increase the deflection capacity, it is necessary to increase the core length of an electromagnet, the number of turns of a coil and the exciting current. Consequently, inductance L1 of the electromagnet 24 in the X-direction first deflector 21 has a large inductance.

On the other hand, the X-direction second deflector 22 can be comprised of comparatively small electromagnets, therefore, inductance L2 of the X-direction second deflection electromagnet 26 can be made smaller than inductance L1 of the X-direction first deflection electromagnet 24. Here, the X-direction first deflection electromagnet 24 and the X-direction second deflection electromagnet 26 are comprised of electromagnets which have same iron core configuration, and the number of turns of coil of the X-direction first deflection electromagnet 24 and that of the X-direction second deflection electromagnet 26 are indicated by N1, N2, respectively. When an irradiation position. X of the particle beam 4 is moved by the distance of ΔX, corresponding changing amount of exciting current of the X-direction first deflection electromagnet 24 is indicated by ΔIX1, and corresponding changing amount of exciting current of the X-direction second deflection electromagnet 26 is indicated by ΔIX2. Under these conditions, the relationship between ΔIX1 and ΔIX2 is expressed by the following mathematical formula;

$$\Delta IX2 = N1/N2 \times \Delta IX1.$$

When the position change ΔX is intended to realize in the same time period: Δt1, the voltage which is required by the X-direction first power source 23 is expressed by the following mathematical formula;

$$V1 = L1 \times \Delta IX1/\Delta t1;$$

and the voltage which is required by the X-direction second power source 25 is expressed by the following mathematical formula;

$$V2 = L2 \times \Delta IX2/\Delta t1.$$

As inductance L of an electromagnet is proportional to the square of the number of turns of coil, $$V2/V1 = L2/L1 * \Delta IX2/\Delta IX1 = (N2/N1)*(N2/N1)*N1/N2$$

$$= N2/N1$$

When iron cores are same, the number of turns of coil N2 which is required by the X-direction second deflection electromagnet 26 is much smaller. Consequently, in order to move the same position change amount ΔX of a particle beam in the same time period: Δt1, when the X-direction second deflector 22 is used, the voltage of a power source is much smaller than that when the X-direction first deflector 21 is used. On the contrary, when a voltage of the X-direction first power source 23 and that of the X-direction second power source 25 are the same, the moving speed of a particle beam which is deflected by the X-direction second deflector 22 can be faster than the moving speed of a particle beam which is deflected by the X-direction first deflector 21. That is, scanning can be performed in a short period.

Further, for example, in a case where a required maximum irradiation range XF is 40 cm, it is necessary for the X-direction first deflection electromagnet 24 to be comprised of electromagnets comprising lamination steel, however, the deflection amount of the X-direction second deflection electromagnet 26 may be small, and therefore its required magnetic field is small. Therefore, the X-direction second deflection electromagnet 26 may be composed of air-core coil, and the configuration of an X-direction second deflection electromagnet 26 is simple. In this case, it is needless to say that the inductance of the X-direction second deflection electromagnet 26 is much smaller than that of the X-direction first deflection electromagnet 24.

Figure 3:
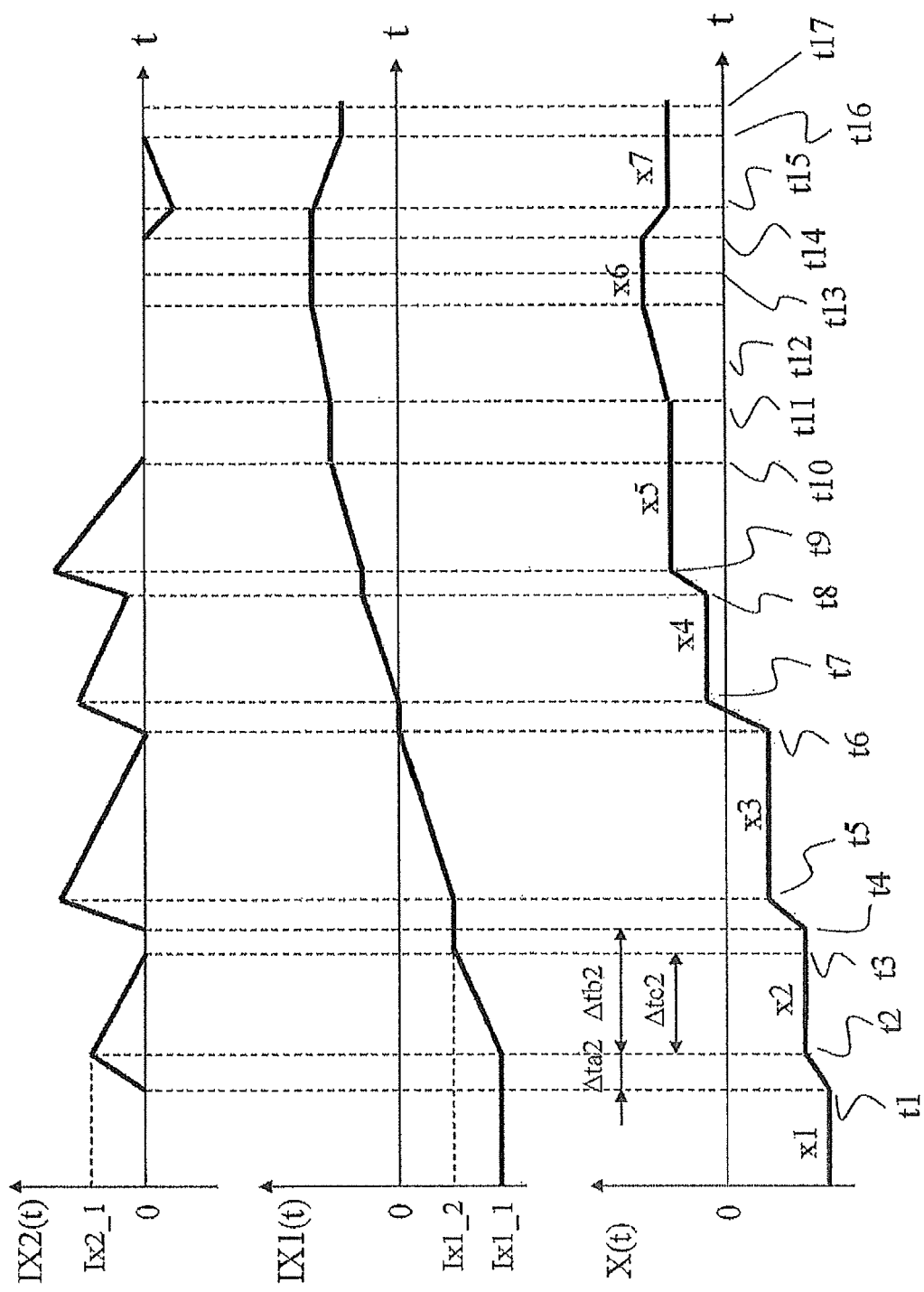
FIG. 3 is a schematic diagram showing the relationship between the motion sequence of an X-direction first deflector and an X-direction second deflector and corresponding time change of a position of particle beam in Embodiment 1 of the present invention.

FIG. 3 is a schematic diagram showing the relationship between the motion sequence of the X-direction first deflector 21 and the X-direction second deflector 22, and corresponding time change of a position of the particle beam 4 in Embodiment 1 of the present invention. In FIG. 3, the horizontal axis indicates the time; t, IX1(t) indicates an electric current of the X-direction first deflection electromagnet 24, IX2(t) indicates an electric current of the X-direction second deflection electromagnet 26, and X(t) indicates an X-direction position of a particle beam in the target 5. X1, X2, . . . and X7 in FIG. 3 correspond to X1, X2, . . . and X7 in FIG. 1, respectively, and indicate spot positions of a particle beam in an X-direction. While the particle beam 4 dwells at each spot position, a planned number of particles are irradiated. The number of particles is controlled by a dose monitor (not shown in FIG.) which can monitor an amount of a particle beam which is irradiated. Further, t1, t2, . . . and t17 indicate change timings of the deflection amount of the X-direction first deflector 21 and the X-direction second deflector 22 (for example, an exciting current of magnet) and an X-direction position of a particle beam.

Next, operation of particle beam irradiation system in Embodiment 1 of the present invention will be described. First, in the therapy planning apparatus 9, a plan of irradiation on the target 5 is prepared. Concretely, a position of a Bragg peak which is formed by the particle beam 4 is scanned in accordance with a three-dimensional shape of the target 5 so as to form a dose range in accordance with a shape of a target. In forming the above-mentioned dose range in accordance with a shape of a target, a spot position (Xi, Yi, Zi) and a radiation dose ni (which is proportional to the number of irradiation particles) at each spot position (Xi, Yi, Zi) are determined. Further, at the same time, in these spot position groups, a set of spot positions corresponding to the same particle beam energy is referred as a spot position in one slice or in one layer.

Figure 4:
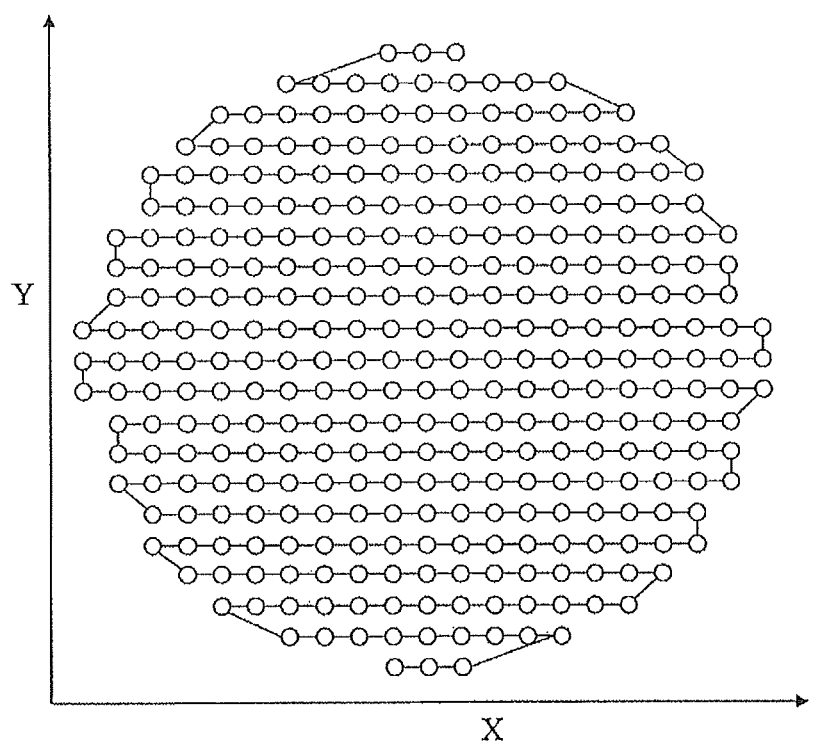
FIG. 4 is a diagram illustrating the arrangement of an example of a spot position of spot scanning irradiation of the present invention.

FIG. 4 is a diagram illustrating the arrangement of spot positions in one slice (one position is indicated by o). These arrangements of spots are determined for each slice, and an irradiation dose ni at each spot position is determined. In total, Kslice pieces of layers are irradiated. As a result, a planned dose is irradiated onto each spot position. In actual irradiation, on one slice, irradiation is performed with same particle beam energy, on another slice, particle beam energy is changed by the particle beam accelerator 6 etc. and then irradiation is performed. That is, spot scan irradiation is performed per layer or per slice. Particle beam energy may be changed by a particle beam accelerator, and it is needless to say that other energy changing means such as a range shifter, ESS (Energy Selection System), or the like may be used.

An example of irradiation operation according to a particle beam irradiation system of the present invention will be described. First, data including irradiation data information (Xi, Yi, ni, jslice, Ebj) at the ith spot position in the jth slice, etc., which is prepared by the therapy planning apparatus 9, is transmitted to the scanning control apparatus 8. Here, Ebj indicates a particle beam energy corresponding to the j th slice. In the scanning control apparatus 8, the data is converted to a setting parameter (Ix1_i,Iy1_i) of the X-direction scanning apparatus 2 and the Y-direction scanning apparatus 3 which corresponds to the irradiation position information (Xi, Yi). Here, Ix1_i indicates an exciting current which is supplied from the X-direction power source 23, which is a driving power source of the X-direction first deflection electromagnet 24, to the X-direction first deflection electromagnet 24 of the X-direction scanning apparatus 2 shown in FIG. 1. In FIG. 1, only the configuration of the X-direction scanning apparatus 2 is shown, however, the Y-direction scanning apparatus 3 also comprises a Y-direction first deflector and a Y-direction second deflector in the same way as that of the X-direction scanning apparatus 2, and Iy1_i corresponds to a setting parameter in a Y-direction first deflector in the Y-direction scanning apparatus 3. Further, in changing a spot position from the ith spot to the i+1th spot, the movement amount in an X-direction is expressed by the following formula; ΔXi=(Xi+1−Xi), and the change amount of a setting parameter in the X-direction first deflector 21 is expressed by the following formula; ΔIx1_i=(Ix1_i+1−Ix1_i). Here, by using the X-direction second deflector 22 in place of the X-direction first deflector 21, in order to realize the same movement amount ΔXi, necessary current change amount ΔIx2_i which is required by the X-direction second power source 25 is preliminarily calculated by the scanning control operation unit 81 or the like, and the obtained data is stored in the scanning control operation unit 81 together with an irradiation setting parameter (Ix1_i). In the same way, regarding a Y-direction, ΔIy2_i is stored.

At the same time, based on a parameter reflected with a result of dose calibration, the data is converted to a monitor unit MUi, which is a counted value of dose monitor (not shown in Fig., in general, a dose monitor is disposed on a particle irradiation system) corresponding to a dose amount ni that is irradiated on each spot position. As above-mentioned, in the scanning control operation unit 81, necessary data for performing irradiation is prepared. The content of the data includes an exciting current parameter (Ix1_i, ΔIx2_i, Iy1_i, ΔIy2_i) and irradiation amount MUi corresponding to a spot position in a slice, an order of irradiation in a slice, particle irradiation beam energy Ebj, j=1, 2, 3 . . . Kslice corresponding to a slice, or the like, per slice on which irradiation is performed.

In the following, as shown in FIG. 1, a case in which a particle beam is scanned in an X-direction will be described. The procedure of scanning in a Y-direction and that of scanning both in an X-direction and a Y-direction are same as that of scanning in an X-direction.

Referring FIG. 1 to FIG. 3, irradiation onto the jth slice will be described. First, the slice number j is transmitted from the scanning control apparatus 8 to the particle beam accelerator 6, the particle beam transport unit 7 and the like, and the apparatuses to which the slice number j is transmitted are set so as to make the energy of a particle beam to be the energy corresponding to the slice number j. Next, the scanning control operation unit 81 transmits an exciting current parameter (Ix1_i, ΔIx2_i), i=1 corresponding to the first spot position X1 in the slice to the beam position movement control operation unit 82 and the beam position holding control operation unit 83, the X-direction first deflector control unit 84 transmits a command to the X-direction first power source 23 so as to set an exciting current Ix1_1. After that, a setting completion signal is transmitted back to the scanning control operation unit 81. When the scanning control operation unit 81 receives the setting completion signal, it transmits a particle beam irradiation start command. When the command is received, the particle beam accelerator 6 or the like emits a particle beam so as to make the particle beam 1 incident on the X-direction scanning apparatus 2 of the particle beam irradiation system 100 via the particle beam transport unit 7 (the particle beam transport unit 7 is not always necessary). The particle beam 1 passes through the X-direction second deflector 22 and the X-direction first deflector 21, and a dose monitor which measures an amount of particle beam dose (not shown in Fig.), etc. and the particle beam 1 is irradiated onto an irradiation position X1 as the particle beam 4. As time passes, the irradiation amount MU_i, i=1 corresponding to X1 position is counted by a dose monitor, when dose amount at the spot dose reaches a planned value, that is, when the irradiation of spot dose is completed, information of dose completion and beam movement command is transmitted to the scanning control apparatus 8 (time t1). At the same time, a dose monitor carries out reset processing of a counter.

When the command is received, the scanning control operation unit 81 transmits a command to the beam position movement control operation unit 82 so as to move the particle beam 4 to the second spot position X2. When the command is received, the X-direction second deflector control unit 85 transmits a command to the X-direction second power source 25 so as to change a current value of exciting current of the X-direction second deflection electromagnet 26 only by ΔIx2_i, i=1 from the present value. In a case shown in FIG. 3, the present current value is zero; therefore, the value of exciting current of the X-direction second deflection electromagnet 26 is changed from zero to Ix2_1. Then, the particle beam 1 is deflected by the X-direction first deflection electromagnet 24 which has been already excited by exciting current of Ix1_1, and the particle beam 1 is also deflected by the X-direction second deflection electromagnet 26, and the spot position is moved from X1 to X2 in time Δta2 at a high speed. Then, the beam position movement control operation unit 82 receives a current change completion command from the X-direction second power source 25 (time t2). When the command is received, the particle beam 4 is irradiated onto a position X2, and the dose monitor restarts counting. It takes time Δtbi, i=2 until a value of the dose monitor reaches a planned dose amount MUi, i=2 corresponding to the position X2. By the time Δtb2, an exciting current of an X-direction first deflection electromagnet 24 is changed at a predetermined speed, and an exciting current of the X-direction second deflection electromagnet 26 is decreased at a predetermined speed so as not for an X position of a particle beam to change. Necessary operation required by the above-mentioned control is performed by the beam position holding control operation unit 83, the X-direction first deflector control unit 84 and the X-direction second deflector control unit 85 transmit a command to power sources, respectively.

As above-mentioned, a particle beam can be made dwell by the control in which the deflection amount which is deflected by the X-direction second deflection electromagnet 26 is gradually substituted by the deflection which is deflected by the X-direction first deflection electromagnet 24, that is, by performing the deflection substitution control. The above-mentioned deflection substitution control is continued until a value of exciting current of the X-direction first deflection electromagnet 24 changes from Ix1_1 to Ix1_2. Further, during the operation of deflection substitution control, the beam position holding control operation unit 83 performs an operation. That is, the exciting current of an X-direction first deflection electromagnet 24 and that of an X-direction first deflection electromagnet 23 is controlled so as for a deviation of an irradiation position of the particle beam 4 from X2 not to be beyond the range of error value that was preliminarily set.

Further, regarding a deflection substitution control, the deflection amount by the X-direction first deflection electromagnet 24 (absolute value of exciting current) may increase as shown in FIG. 3, in t7 to t8 or in t9 to t10 or may decrease as shown in FIG. 3, in t2 to t3, in t5 to t6, in t9 to t10 or in t15 to t16. That is, in a deflection substitution control, the deflection amount by the X-direction first deflection electromagnet 24 is increased or decreased, that is, the deflection amount is changed. On the other hand, regarding a deflection substitution control by the X-direction second deflection electromagnet 26, as shown in FIG. 3, in t2 to t3, in t5 to t6, in t7 to t8, in t9 to 10 or in t15 to t16, the deflection amount (absolute value of exciting current) is always decreased.

For example, in order to make same position change at each X-direction position, the exciting current change amounts which are required for the X-direction first deflection electromagnet 24 and the X-direction second deflection electromagnet 26 are preliminarily calculated or measured, and the obtained values can be used as parameters of the beam position holding control operation unit 83. Then, as time $\Delta tc2$ passes, (time t3,) the value of exciting current of the X-direction first deflection electromagnet becomes the value Ix1_2 corresponding to the present irradiation position X2. Here, $\Delta tc2 < \Delta tb2$. Then, a dose monitor counts the irradiation amount MUi, i=2 corresponding to irradiation position X2, and transmits information of dose completion and a spot position movement command to the scanning control operation unit 81 (in time t4). In a particle beam irradiation system, so as to reduce error dose and shorten irradiation time, it is required for a spot position to be moved at a high speed, therefore, effective scanning speed in an X-direction is set to be high speed, for example, 10 cm/msec. Depending on dose applied on a target, as supposed time for above-mentioned various time, for example, an irradiation time $\Delta tb$ is in a range of 1 msec to 20 ms, moving time $\Delta t$ a is 40 μs when moving amount is 5 mm. That is, an irradiation time $\Delta tb$ in one spot position is approximately 25 times longer than moving time $\Delta t$ a. Consequently, a current change in the X-direction first power source 23 can be made much slower than scanning speed.

The above-mentioned operation is repeatedly performed for all scanning position spots in the jth slice. Then, when applying irradiation to all spot positions in a slice is completed, the scanning control apparatus 8 transmits a command to the particle beam accelerator 6 or the like to stop the particle beam 1. Then, the scanning control apparatus 8 radiates a particle beam onto the j+1 th slice by the same irradiation method as that for the jth slice. As above-mentioned, the operation is repeated until applying irradiation to all K slices is completed.

As above-mentioned, a particle beam can be irradiated onto a predetermined irradiation position in the target 5 which is determined by the therapy planning apparatus 9, and dose distribution in accordance with three-dimensional shape of a target such as a tumor can be formed. Further, in the above description, only a position change of an X-direction is described, however, a position change in a Y-direction is also performed in the same way as that of a position change in an X-direction. Further, in the above description, a case where both of the X-direction scanning apparatus 2 and the Y-direction scanning apparatus 3 are comprised of two deflectors, however, the configuration in which Y-direction scanning apparatus 3 has only one deflector and scanning is performed without substitution control in a Y-direction may be acceptable.

Here, necessary power capacity in a case where high speed deflection is realized only by an X-direction first deflector, and necessary power capacity in a case where high speed deflection is realized by an X-direction second deflector so as to perform deflection substitution control in the present invention is compared. When the ratio N1/N2, that is, the ratio of the number of winding of an X-direction first deflection electromagnet and the number of winding of an X-direction second deflection electromagnet is 10, in order to change the same deflection amount in the same change time $\Delta t1$, the relationship between the necessary voltage of an X-direction first power source V1 and the necessary voltage of an X-direction second power source V2 is $$V1 = N1/N2 * V2 = 10 * V2,$$

as above-mentioned. In order to obtain the same deflection change amount by an X-direction first deflection electromagnet and an X-direction second deflection electromagnet, the amount of change of magnetic flux, that is, the value obtained by multiplying the number of winding by the amount of change of current should be the same. Consequently, $$\Delta IX2 = 10 * \Delta IX1$$

When $\Delta IX1$ is 10 A and V1 is 100V, V2 is 10V and $\Delta IX2$ is 100 A. In an X-direction first deflector, it is required for current to increase from the state where current has already flowed. For example, when the above-mentioned XF is approximately ten times as large as $\Delta X1$, in a part in the vicinity where the maximum deflection is generated, for example, approximately 100 A of exciting current is flowing in an X-direction first deflection electromagnet. Consequently, in order to increase the current in the part in the vicinity where the maximum deflection is generated by 10 A, it is required for a current to increase, for example, from 90 A to 100 A. On the other hand, a current in an X-direction second deflection electromagnet is not flowing at first; therefore, a current may be increased from 0 A to 10 A. In a case where the deflection amount is changed in time $\Delta t1$, in order to change the deflection amount only by an X-direction first deflector, a power source of 100V*100A=10 KVA is required as an X-direction first power source. On the other hand, in a case where an X-direction second deflector is used, an X-direction second power source may be 10V*100 A=1 KVA Even when an X-direction second deflector is used, an X-direction first deflector is required, however, at maximum, the deflection amount may be changed in time, for example, ten times as long as that of time $\Delta t1$. Consequently, required voltage of an X-direction first power source is one-tenth of the above-mentioned value, that is, 10V, and power source of 10V*100 A=1 KVA may be required as an X-direction first power source. Consequently, in a case where high speed deflection is realized by using an X-direction second deflector, an X-direction first power source may be 1 KVA and an X-direction second power source may be 1 KVA, as total, power source of 2 KVA may be required. As above-mentioned, when the change of deflection amount is intended to realize at a high speed only by using an X-direction first deflector, a power source having capacity that is five times as much as that when an X-direction second deflector is used together with the X-direction first deflector is required.

As described in the above, even in a case where an irradiation field is large (maximum widths of scanning in an X-direction and a Y-direction are large), when two deflectors, that is, a second deflector which can make only small amount of deflection but operate at a high speed and a second deflector which operates at low speed but can make large deflection are provided, movement of a spot position can be performed at a high speed even a voltage of power source of a deflection electromagnet is low. Consequently, whole irradiation time can be shortened by using a scanning power source having small capacity. In a particle beam therapy system corresponding to applying large radiation to a large tumor as an objective, the effect such that high speed scanning and applying radiation onto a large irradiation field can be performed by a power source having small capacity is especially remarkable. Further, when scanning speed of a first deflector can be reduced, there is an effect such that heat generation and magnetic field delay caused by an eddy current which is generated in an alternating current electromagnet can be reduced. As a result, reliability of particle beam irradiation system can be enhanced, reduction of system in size can be realized, and irradiation accuracy can be improved.

FIG. 3 shows an exciting current $IX1(t)$ of the X-direction first deflection electromagnet 24 and an exciting current $IX2(t)$ of the X-direction second deflection electromagnet 26 at a spot position from X1 to X7, and change of corresponding spot position $X(t)$ in accordance with time. A case where an exciting current IX2 of the X-direction second deflection electromagnet 26 can be returned to zero at spot positions X2 and X3 in a deflection substitution control is shown. At a spot position X4, a spot position moving command is received before the exciting current IX2 is returned to zero, therefore, Ix2 is increased to be a predetermined value Ix2_4 from the state in which Ix2 is not zero, during the next irradiation of X5, Ix2 is returned to zero. As above-mentioned, Ix2 may not be returned to zero by one performance of deflection substitution control. It is acceptable for Ix2 to be returned to zero by multiple performances of deflection substitution control such as twice, three times or the like. However, it is required for IX2 not to exceed a rated current value of an X-direction second power source 25.

Further, it may take time for a beam position to move form a spot position X5 to X6, therefore movement of beam position is performed only by using an X-direction first deflector 21 without performing deflection substitution control. As above-mentioned, in actual scanning irradiation, before starting the irradiation, the maximum time that is required for applying radiation onto each spot position is calculated considering average value of beam current of accelerator and time change. Then, in a case where an irradiation time is shorter than a predetermined time, deflection substitution control on that spot can be skipped. That is, when a current change speed which is required by the X-direction first power source 23 is lower than a predetermined value, a beam may be moved to the next spot position only by change of a deflection amount of the X-direction first deflection electromagnet 24. In this case, beam position movement can be performed only by using the X-direction first deflection apparatus 21 without performing deflection substitution control. In this case, an exciting current of the X-direction second deflection electromagnet 26 of a high speed deflector may not be returned to zero, however, there is no problem when the difference between a maximum possible amount of exciting current of the X-direction second deflection electromagnet 26 and a residual amount of exciting current is larger than $\Delta Ix2\_i$ which is required value for moving to the next irradiation position. That is, a rated value of maximum exciting current of the X-direction second power source 25 may be set so as to secure the sufficient value to perform operation of moving the distance of several spots. In a case where a particle beam irradiation system is configured as above mentioned, even in a case where the number of planned irradiation dose onto each irradiation position in a same slice varies in a large range, a deflection substitution control during irradiation can be accurately performed, and a particle beam irradiation system having high reliability can be provided.

Further, in FIG. 3, from time t1 to t2, t3 to t4, or the like, an exciting current of an X-direction first deflection electromagnet IX1 is not changed, however, during the above-mentioned period, IX1 may be changed. In this case, the change amount of an exciting current of an X-direction second deflection electromagnet IX2 is smaller than that described in FIG. 3. Alternatively, by making the change amount of an exciting current of an X-direction second deflection electromagnet IX2 to be the same as that described in FIG. 3, movement of a beam position can be performed at higher speed.

Further, in the same way as that of operation at time t8 in FIG. 3, in a case where a dose monitor counts the dose completion during the deflection substitution control, and an irradiation position movement command is outputted from the beam position movement control operation unit 82, the beam position holding control operation unit 83 may immediately interrupts the deflection substitution control command, and the movement control of an irradiation position may be started by the beam position movement control operation unit 82. In this case, an excitation current of the X-direction second deflector 22, which is a high-speed deflector, is not returned to zero. However, there is no problem when the difference between the maximum value of capable of exciting of the X-direction second power source 25 and the residual amount of excitation current at present is larger than $\Delta Ix2\_i$ which is necessary to move a particle beam to next irradiation position. That is, the irradiation system may be designed such that the maximum excitation current rated value of the X-direction second power source 25 can acquire the sufficient value to move a particle beam by a distance equivalent to several spots. In a case where a particle beam irradiation system is configured as above mentioned, even in a case where the time change of a beam current of the particle beam 1 is large, the particle beam can be irradiated on a target accurately. Consequently, a reliable particle beam irradiation system can be provided.

In FIG. 1, the X-direction second deflection electromagnet 26 and the X-direction first deflection electromagnet 24 are disposed in this order along the traveling direction of the particle beam 1, however, when the order of disposition is reverse, the same effect of this invention can be obtained. Further, when the X-direction first deflection electromagnet 24 and the X-direction second deflection electromagnet 26 are sufficiently separately disposed so as not for magnetic fields to influence each other, the inductance viewed from the X-direction second power source 25 can be decreased, and in addition to that, the amount of eddy current, which is generated by high-speed change magnetic field of the X-direction second deflection electromagnet 26 and given to a conductive constituent of the X-direction first deflector 21, can be decreased.

Further, the X-direction second deflection electromagnet 26 may comprise an electromagnet with an iron core (Ferrite core, lamination steel, etc.), however, even in a case where the X-direction deflection electromagnet 26 comprises an air-core coil without an iron core, an effect of this invention can be obtained. Further, the X-direction second deflector may have the configuration such that not the deflection, which is generated by a magnetic field using an electromagnet, but the deflection, which is generated by an electric field using a deflection electrode which generates an electric field, is utilized.

Embodiment 2

Figure 5:
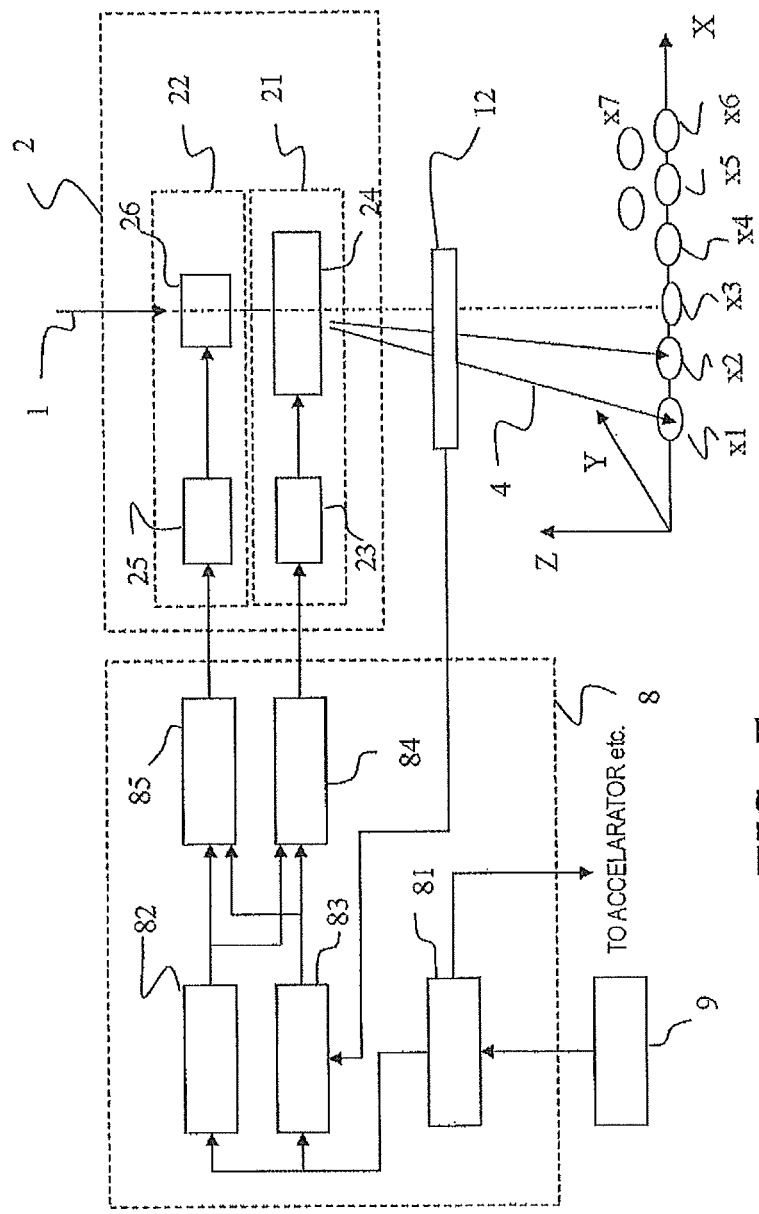
FIG. 5 is a block diagram illustrating the configuration of a particle beam irradiation system according to Embodiment 2 of the present invention.

FIG. 5 is a block diagram illustrating the configuration of a particle beam irradiation system according to Embodiment 2 of the present invention. In FIG. 5, reference character 12 denotes a beam position monitor. The configuration and operation of a particle beam irradiation system according to Embodiment 2 is same as that of Embodiment 1 that was described in the above except that position information of the beam position monitor 12 is fed back to the scanning control apparatus 8 so as to prevent the deviation of an irradiation position of a particle beam 4.

In FIG. 5, when a beam position holding control operation unit 83 performs deflection substitution control, an exciting current which is supplied by an X-direction second power source 25 and an exciting current which is supplied by an X-direction first power source 23 are controlled at the same time or alternately so as to substitute the deflection. In performing the above-mentioned operation, position information, which is transmitted from the beam position monitor 12 which monitors a position of the particle beam 4 which is deflected by both of an X-direction second deflection electromagnet 26 and an X-direction first deflection electromagnet 24, is inputted to the beam position holding control operation unit 83. In performing deflection substitution control, the beam position holding control operation unit 83 transmits a command to perform a feedback control of both of the X-direction second deflector 22 and the X-direction first deflector 21 or either one of them in accordance with position information which is transmitted from the beam position monitor 12 so as to prevent deviation of an irradiation position of the particle beam 4 from a planned position.

In particular, an irradiation position of a particle beam can be maintained accurately during applying irradiation and a particle beam can be irradiated precisely by performing feedback control of the X-direction second deflector 22 which can operate at a high speed by using position information which is transmitted from the beam position monitor 12. As above-mentioned, when not a feedback control of a first deflector but a feedback control of a second deflector which can operate at a high speed is performed by using position information which is transmitted from the beam position monitor 12, feedback control with high accuracy can be performed with respect to a position error which changes rapidly according to time. Consequently, a planned dose distribution can be formed precisely in a target area.

Embodiment 3

Figure 6:
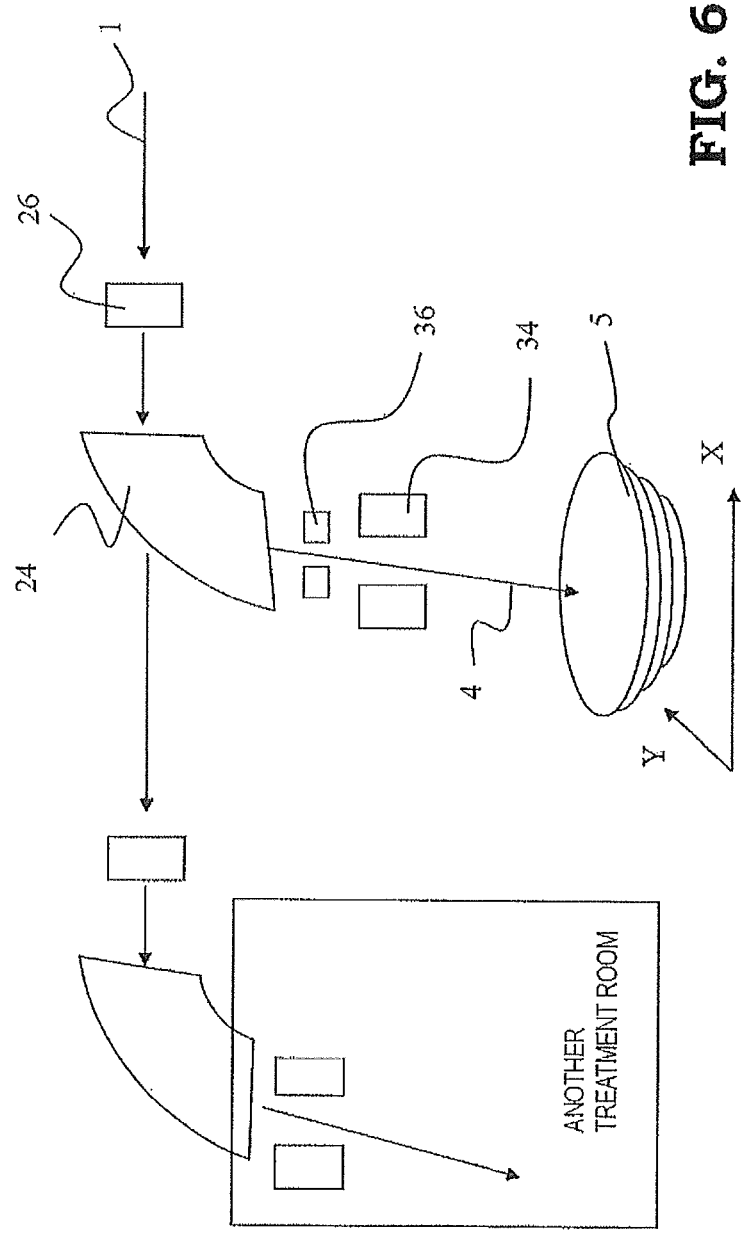
FIG. 6 is a block diagram illustrating the configuration of a particle beam irradiation system according to Embodiment 3 of the present invention.

FIG. 6 is a block diagram illustrating the configuration of a particle beam irradiation system according to Embodiment 3 of the present invention. The configuration and operation of a particle beam irradiation system according to Embodiment 3 of the present invention will be described with reference to FIG. 6. In FIG. 6, same reference characters as those in FIG. 1 denote same or equivalent elements. Reference character 24 denotes a deflection electromagnet which deflects a main direction of particle beam traveling so as to guide the particle beam to a target (for example, a deflection electromagnet which guides a beam to respective therapy rooms, Bending-Magnet which guides a beam to a patient or the like), and at the same time, the deflection electromagnet 24 also functions as an X-direction first deflection electromagnet. Reference character 26 denotes an X-direction second deflection electromagnet. Reference character 34 denotes a Y-direction first deflection electromagnet, and reference character 36 denotes a Y-direction second deflection electromagnet. Further, a scanning control apparatus is not shown in FIG. 6, however, a scanning control apparatus which was described in Embodiment 1 and Embodiment 2 is provided in a particle beam irradiation system according to Embodiment 3.

The configuration and operation of a particle beam irradiation system according to Embodiment 3 is basically same as that of Embodiment 1 that was described in the above except for the following description. In FIG. 6, the particle beam deflection electromagnet 24 functions also as an X-direction first deflection electromagnet. In comparison with Embodiment 1, the X-direction first deflection electromagnet 24 is a large electromagnet which can deflect a particle beam at a large deflection angle. Therefore, it is difficult to change an X-direction position of a particle beam 4 at a high speed by using only the X-direction first deflection electromagnet 24. Therefore, both of the X-direction second deflection electromagnet 26 and the X-direction first deflection electromagnet 24 are used for performing deflection substitution control. The X-direction second deflection electromagnet 26 is used for moving a particle beam position at a high speed in the same way as described in Embodiment 1, a deflection amount of the X-direction second deflection electromagnet 26 is decreased gradually and a deflection amount of the X-direction first deflection electromagnet 24 is changed gradually at the same while a particle beam is irradiated when the particle beam 4 is at a predetermined position. As above-mentioned, deflection substitution control is performed so as not to change substantially an irradiation position of the particle beam 4 during applying irradiation. Regarding a Y-direction, in the same way as that of an X-direction, the Y-direction second deflection electromagnet 36 functions to move a spot position of the particle beam 4 in a Y-direction at a high speed, a deflection amount of the Y-direction second deflection electromagnet 36 is decreased gradually and a deflection amount of the Y-direction first deflection electromagnet 34 is changed gradually while irradiation is applied at a predetermined Y position. As above-mentioned, deflection substitution control is performed so as not to change substantially the Y position of the particle beam 4 during applying irradiation. As above-mentioned, irradiation can be applied to the target 5 by scanning a particle beam at a high speed.

In Embodiment 3, a deflection electromagnet which transports a particle beam to respective therapy rooms is used as the X-direction first deflection electromagnet 24. Therefore, a particle beam irradiation system according to the present invention can be realized without increasing the number of electromagnet which is required by a particle beam irradiation system. Further, it is not necessary to dispose an X-direction scanning apparatus between a deflection electromagnet which also functions as the X-direction first deflection electromagnet 24 and the target 5. Therefore, an irradiation nozzle can be miniaturized (a length of an irradiation nozzle can be shortened). Consequently, a particle beam irradiation system can be reduced in size. Further, in Embodiment 3, in a case where irradiation is applied in the scanning order in which an X-direction and a Y-direction shown in FIG. 4 are changed, on the average, the time period in which a position of the particle beam 4 in an X-direction is constant is longer. Therefore, it can take longer time to perform deflection substitution control in an X-direction. Consequently, even in a case where the X-direction first deflection electromagnet 24 is a large electromagnet (in general, inductance is also large), a required maximum voltage of an X-direction first deflection electromagnet 24 may be small. Consequently, a particle beam irradiation system according to the present invention can be realized by using a power source having small capacity.

Further, in a case where the X-direction first deflection electromagnet 24 is a deflection magnet, when a magnetic pole end is configured to have a predetermined angle, a particle beam which is scanned by the X-direction second deflection electromagnet 26 and the X-direction first deflection electromagnet 24 can be irradiated perpendicularly onto the target 5.

Embodiment 4

Figure 7:
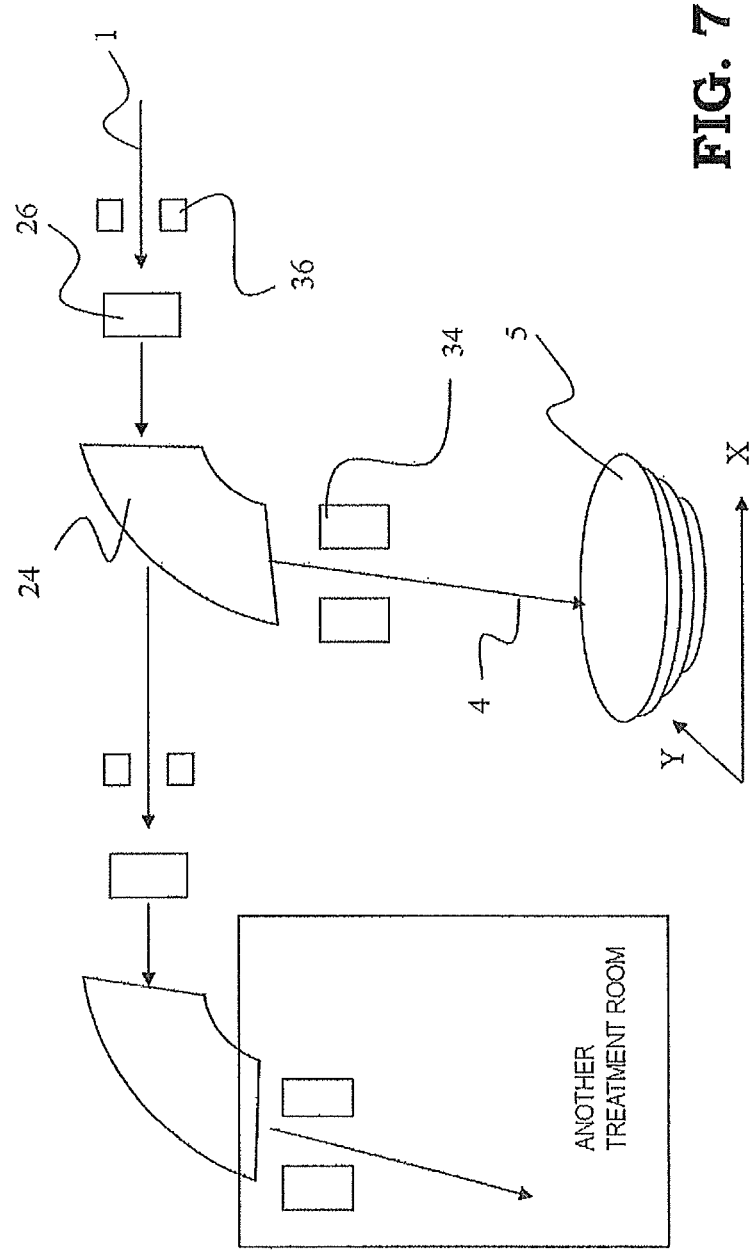
FIG. 7 is a block diagram illustrating the configuration of a particle beam irradiation system according to Embodiment 4 of the present invention.

FIG. 7 is a block diagram illustrating the configuration of a particle beam irradiation system according to Embodiment 4 of the present invention. In FIG. 7, the same reference characters as those in FIG. 1 and FIG. 6 denote the same or equivalent elements. Unlike Embodiment 3 (the configuration shown in FIG. 6), in Embodiment 4 a Y-direction second deflection electromagnet 36 is disposed at the upstream of a deflection electromagnet 24 which functions as an X-direction first deflection electromagnet and deflects a main direction of a particle beam traveling so as to guide the particle beam to a target. Further, in FIG. 7, a scanning control apparatus is not shown, however, a scanning control apparatus that was described in Embodiment 1 and Embodiment 2 is disposed in a particle beam irradiation system according to Embodiment 4.

As shown in FIG. 7, as the Y-direction second deflection electromagnet 36 is disposed at the upstream of the X-direction first deflection electromagnet 24, it is not necessary to increase the distance between the X-direction first deflection electromagnet 24 and the target 5. Therefore, a length of an irradiation nozzle can be made shorter than that of the configuration of Embodiment 3 shown in FIG. 6. As a result, a particle beam irradiation system can be reduced in size. Further, the Y-direction second deflection electromagnet 36 can be disposed away from the target 5. As a position change amount is proportion to a deflection angle and the distance between a deflection magnet and an irradiation position, according to Embodiment 4, a required current change amount of a power source of the Y-direction second deflection electromagnet 36 which makes a predetermined Y-direction position change $\Delta Y_i$ may be small. Therefore, a power source of the Y-direction second deflection electromagnet 36 can be miniaturized.

Embodiment 5

Figure 8:
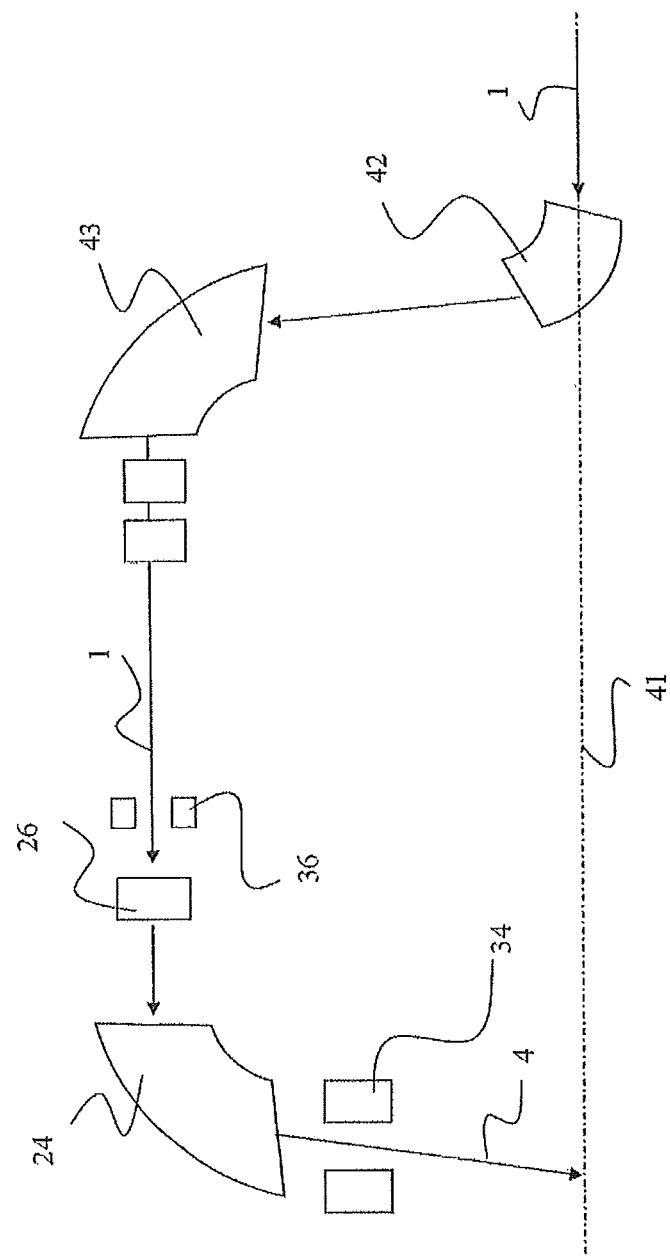
FIG. 8 is a block diagram illustrating the configuration of a particle beam irradiation system according to Embodiment 5 of the present invention.

FIG. 8 is a block diagram illustrating the configuration of a particle beam irradiation system according to Embodiment 5 of the present invention. In FIG. 8, the same reference numerals as those in FIG. 1 and FIG. 7 denote the same or equivalent elements. The configuration according to Embodiment 5 is different from that of Embodiment 4, that is, the configuration shown in FIG. 7 is such that a particle beam irradiation system is configured as a rotating gantry. Reference character 42 denotes a second rotating gantry deflection electromagnet, on a predetermined deflection plane, a particle beam 1 is deflected once from a traveling direction of an incident particle beam so as to be incident on a first rotating gantry deflection electromagnet 43, then the particle beam 1 is deflected by the first rotating gantry deflection electromagnet 43 to a direction parallel to a traveling direction of a particle beam which is incident on the second rotating gantry deflection electromagnet 42 in the same deflection plane. After that, the particle beam is made incident on a Y-direction second deflection electromagnet 36 and an X-direction second deflection electromagnet 26, and is deflected by a deflection electromagnet 24 which is the last electromagnet in a rotating gantry, and then a particle beam 4 is irradiated onto a patient. Further, the deflection electromagnet 24 also functions as an X-direction first electromagnet. Reference character 34 denotes a Y-direction first deflection electromagnet. Then, all of configuration elements shown in FIG. 8 are fixed to a same structure that can rotate around a gantry rotating axis 41 (which is disposed at approximately horizontal direction). A particle beam irradiation system comprising the above-mentioned structure and configuration elements shown in FIG. 8 is referred as a rotating gantry.

In Embodiment 5, a Y-direction deflection electromagnet and an X-direction deflection electromagnet which are used for scanning the particle beam 1 toward a target so as to realize a three-dimensional radiation are stored in a rotating gantry. In Embodiment 5, the deflection electromagnet 24 which is the last deflection electromagnet in a rotating gantry functions also as an X-direction first deflection electromagnet which is a configuration element of a particle beam scanning apparatus in an X-direction. Further, in the downstream of the deflection electromagnet 24 which is the last deflection in the rotating gantry, an electromagnet 34 of a Y-direction first deflector is disposed. The X-direction second deflection electromagnet 26 and the Y-direction second deflection electromagnet 36, which are necessary to perform a high-speed scanning, are disposed at the upstream of the deflection electromagnet 24 which is the last deflection electromagnet in the rotating gantry. That is, the X-direction second deflection electromagnet 26 and the Y-direction second deflection electromagnet 36 are disposed at an incident side of a particle beam.

When a spot scan irradiation is performed in which the particle beam is toward the target 5 by using a particle beam irradiation system according to Embodiment 5 of the present invention, first, a rotating angle of rotating gantry is set in accordance with an irradiation angle which is preliminarily determined by a treatment plan, and an angle of rotating gantry, a position and an angle of therapy table (not shown in Fig.) are set. Then, as described in Embodiment 1, the target 5 is irradiated per slice. In the procedure, operation of an X-direction first deflector, an X-direction second deflector, a Y-direction first deflector, a Y-direction second deflector and a scanning control apparatus in Embodiment 5 is basically same as that in Embodiment 1.

In Embodiment 5, the deflection electromagnet 24 which is disposed in the last in the rotating gantry is used as an X-direction first deflection electromagnet, and an X-direction second deflection electromagnet and a Y-direction second deflection electromagnet are disposed at the upstream of the deflection electromagnet 24 which is disposed in the last in the rotating gantry. Therefore, it is not required to increase the length of an irradiation nozzle of rotating gantry. Consequently, in addition to the above-mentioned effect of embodiment, as shown in FIG. 8, the present invention can be realized without increasing the radius of rotation (height) of rotating gantry, and increasing of a particle beam radiation system in size can be suppressed. As a result, the present invention can contribute to the widespread use of particle beam treatment apparatus mounting a particle beam irradiation system.

Further, in Embodiment 5, a case where the X-direction second deflecting electromagnet 26 and the Y-direction second deflecting electromagnet 36 are disposed at the upstream of a deflection electromagnet which is disposed in the last in the rotating gantry was described, however, it is needless to say that even in a case where both of the X-direction second deflection electromagnet 26 and the Y-direction second deflection electromagnet 36 or either one of them is disposed on the downstream of the deflection electromagnet 24 which is disposed in the last in the rotating gantry, the effect of the present invention, that is, high-speed scanning can be realized.

Embodiment 6

Figure 9:
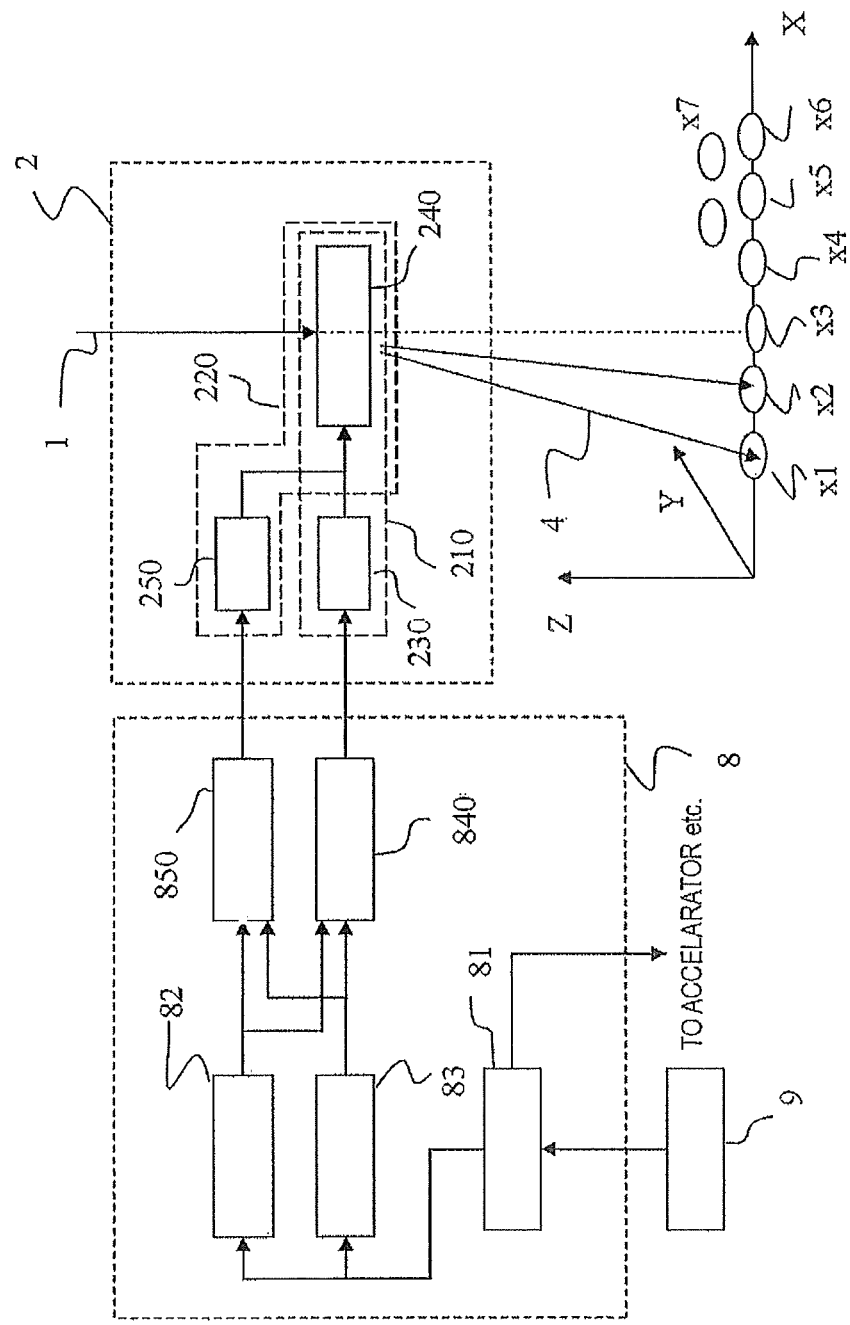
FIG. 9 is a block diagram illustrating the configuration of a particle beam irradiation system according to Embodiment 6 of the present invention.

FIG. 9 is a block diagram illustrating the configuration of a particle beam irradiation system according to Embodiment 6 of the present invention. In FIG. 9, the same reference numerals as those in FIG. 1 denote the same or equivalent elements. In Embodiment 6, as a deflection electromagnet which deflects a particle beam 1 in the X direction, only an X-direction deflection electromagnet 240 is disposed. There exists only one excitation coil in the X-direction deflection electromagnet 240; however, this single excitation coil is driven by two power sources, i.e., an X-direction first power source 230 and an X-direction second power source 250. As is the case with an X-direction first deflection electromagnet 24 in Embodiment 1 and 2, the X-direction deflection electromagnet 240 has a capability of deflecting the particle beam 1 up to the maximum width of a target. The X-direction first power source 230 is a power source which can output a large current, but is low-voltage and hence cannot rapidly change the current because the inductance of the excitation coil of the X-direction deflection electromagnet 240 is large; that is to say, the X-direction first power source 230 is a low-voltage large-current power source. The X-direction second power source 250 is a high-voltage small-current power source, the value of a current which can output is small, but which can rapidly change the current even when the inductance of the excitation coil of the X-direction deflection electromagnet 240 is large. The current from the X-direction first power source 230 and the current from the X-direction second power source 250 are superimposed on each other and flow in the excitation coil of the X-direction deflection electromagnet 240.

In the particle beam irradiation system according to Embodiment 6, the X-direction first power source 230 and the X-direction deflection electromagnet 240 perform the operation corresponding to the operation of the X-direction first deflector 21 explained in Embodiment 1 and 2; and the X-direction second power source 250 and the X-direction deflection electromagnet 240 perform the operation corresponding to the operation of the X-direction second deflector 22 explained in Embodiment 1 and 2. That is, as shown in FIG. 9, an X-direction first deflector 210 comprises the X-direction first power source 230 and the X-direction deflection electromagnet 240, and an X-direction second deflector 220 comprises the X-direction second power source 250 and the X-direction deflection electromagnet 240. The X-direction deflection electromagnet 240 functions as an electromagnet of the X-direction first deflector 210 and that of the X-direction second deflector 220. When the particle beam 1 is moved between adjacent spot positions in spot scanning irradiation, the deflection of the particle beam 1 is changed by rapidly changing the excitation current of the excitation coil of the X-direction deflection electromagnet 240 by the X-direction second power source 250. After that, the excitation current of the X-direction deflection electromagnet 240 which is generated by the X-direction second power source 250 is gradually substituted to the excitation current which is generated by the X-direction first power source 230, and the excitation current which is superimposed by the X-direction first power source 230 and the X-direction second power source 250 is controlled so as to be constant. By performing the above-mentioned, a particle beam is made dwell so as to irradiate the particle beam on a target. As described above, in the same way as that explained in Embodiment 1 and 2, when a particle beam is moved, a deflection amount of the X-direction second deflector 220 is increased so as to move the particle beam, and when the particle beam is made dwell, a deflection amount of the X-direction second deflector 220 is substituted to the deflection which is generated by the X-direction first deflector 210. That is, substitution control is performed.

Further, in the above, only the X-direction scanning apparatus 2 was explained, however, it is needles to say such that a Y-direction scanning apparatus 3 may comprise one deflection electromagnet and two power sources in the same way as that of the X-direction scanning apparatus 2 shown in FIG. 9. However, the Y-direction scanning apparatus 3 may comprise only one deflector and may be the configuration such that scanning is performed without performing substitution control.

As described above, in Embodiment 6, only one deflection electromagnet for deflecting a particle beam is disposed and an excitation coil of the deflection electromagnet is driven by two power sources so as to perform substitution control in spot scanning irradiation which was explained in Embodiment 1 and 2. Consequently, even in a case where an irradiation field is large (maximum widths of scanning in an X-direction and in a Y-direction are large), by driving one deflection electromagnet by two power sources, that is, one power source which can operate at a high speed and another power source which can drive large current though the changing speed of the excitation current is slow, a spot position can be moved at a high speed, and whole irradiation time can be shorten by a low-capacity power source as a whole.

Embodiment 7

Figure 10:
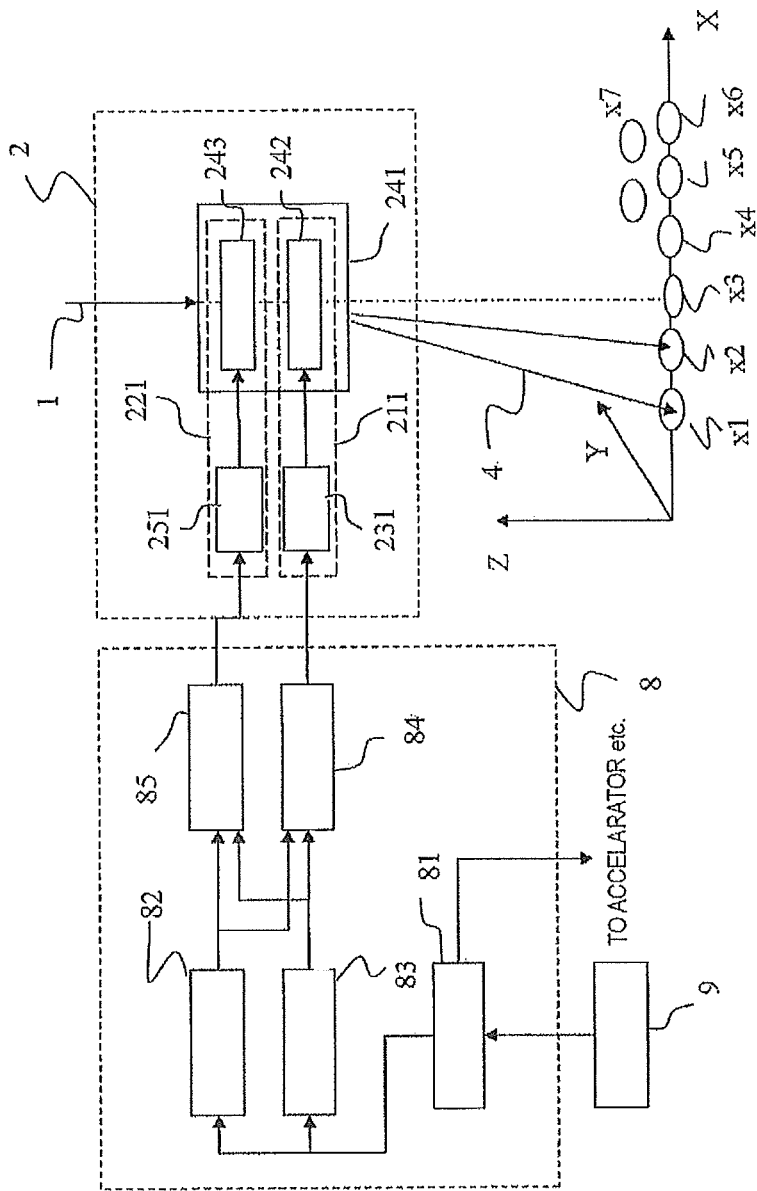
FIG. 10 is a block diagram illustrating the configuration of a particle beam irradiation system according to Embodiment 7 of the present invention.

FIG. 10 is a block diagram illustrating the configuration of a particle beam irradiation system according to Embodiment 7 of the present invention. In FIG. 10, the same reference numerals as those in FIG. 1 denote the same or equivalent elements. In Embodiment 7, in an X-direction scanning apparatus 2, as an electromagnet for deflecting a particle beam 1 in the X-direction, only an X-direction deflection electromagnet 241 is disposed. However, an X-direction deflection electromagnet 241 is formed in such a way that two excitation coils, i.e., a first X-direction excitation coil 242 and a second X-direction excitation coil 243 are wound around a single and the same iron core. The number of coil turns of the first X-direction excitation coil 242 is larger than that of the second X-direction excitation coil 243; thus, the first X-direction excitation coil 242 has a large inductance, and the second X-direction excitation coil 243 has a small inductance. The first excitation coil 242 is driven by a first power source 231, and the second excitation coil 243 is driven by a second power source 251.

The range of scanning which can be performed in such a way that the first excitation coil 242 driven by the X-direction first power source 231 energizes the X-direction deflection electromagnet 241 so that the particle beam 1 is deflected is the same as the range of deflection which can be performed by the X-direction first deflection electromagnet in Embodiment 1 and 2. The range of scanning which can be performed in such a way that the second excitation coil 243 driven by the X-direction second power source 251 energizes the X-direction deflection electromagnet 241 so that the particle beam 1 is deflected is the same as the range of deflection which can be performed by the X-direction second electromagnet in Embodiment 1 and 2. That is to say, by the first excitation coil 242 driven by the X-direction first power source 231, the particle beam 1 can be largely deflected, but the particle beam can not be scanned at a high speed. By the second excitation coil 243 driven by the X-direction second power source 251, the particle beam 1 can be scanned at a high speed, but the particle beam 1 can not be largely deflected.

In the particle beam irradiation system according to Embodiment 7, the first excitation coil 242 and the X-direction first power source 231 perform the operation corresponding to the operation of an X-direction first deflector 21 explained in Embodiment 1 and 2, and the second excitation coil 242 and the X-direction second power source 251 perform the operation corresponding to the operation of an X-direction second deflector 22 explained in Embodiment 1 and 2. That is, as shown in FIG. 10, an X-direction first deflector 211 comprises the first excitation coil 242 and the X-direction first power source 231, and an X-direction second deflector 221 comprises the second excitation coil 243 and the X-direction second power source 251. When the particle beam 1 is moved between adjacent spot positions in spot scanning irradiation, the second excitation coil 243 is driven by the x-direction second power source 251 so as to deflect the particle beam 1. After that, the deflection which is generated by the excitation by the second excitation coil 243 is gradually substituted to the deflection which is generated by the excitation by the first excitation coil 242, that is, deflection substitution control is performed. By performing the above-mentioned deflection substitution control, a particle beam is made dwell so as to irradiate the particle beam on a target.

Further, in the above, only the X-direction scanning apparatus 2 was explained, however, it is needles to say such that a Y-direction scanning apparatus 3 may comprise one deflection electromagnet and two power sources in the same way as that of the X-direction scanning apparatus 2 shown in FIG. 10. However, the Y-direction scanning apparatus 3 may comprise only one deflector and may be the configuration such that scanning is performed without performing substitution control.

As described above, in Embodiment 7, two excitation coils having different number of coil turns are disposed at an iron core of a deflection electromagnet which deflects a particle beam, and the two excitation coils are driven by their own power sources. By the above-mentioned configuration, substitution control in spot scanning irradiation which was explained in Embodiment 1 and 2 is performed. Consequently, even in a case where an irradiation field is large (maximum widths of scanning in an X-direction and in a Y-direction are large), by disposing two excitation coils, that is, a second excitation coil, which generates small amount of deflection but has small inductance and is driven by a driving power source which can operated at a high speed, and a first excitation coil, which scans at a slow speed but which can generate large deflection, at one deflection electromagnet, a spot position can be moved at a high speed, and whole irradiation time can be shorten by a low-capacity power source as a whole.

DESCRIPTION OF THE REFERENCE NUMERALS

1: particle beam
2: X-direction scanning apparatus
3: Y-direction scanning apparatus
4: scanned particle beam
5: target
6: accelerator
7: particle beam transport unit
8: scanning control apparatus
9: therapy planning apparatus
12: beam position monitor
21, 210, 211: X-direction first deflector
22, 220, 221: X-direction second deflector
23, 230, 231: X-direction first power source
24: X-direction first deflection electromagnet
240, 241: X-direction deflection electromagnet
242: first excitation coil
243: second excitation coil
25, 250, 251: X-direction second power source
26: X-direction second deflection electromagnet
31: Y-direction second deflector
32: Y-direction first deflector
41: rotating gantry rotation axis
42: second rotating gantry deflection electromagnet
43: first rotating gantry deflection electromagnet
281: scanning control operation unit
82: beam position movement control operation unit
83: beam position holding control operation unit
84: X-direction first deflector control unit
85: X-direction second deflector control unit
100: particle irradiation system

The invention claimed is:

1. A particle irradiation system for repeating an operation of moving an incident particle beam along a first axis and for making the incident particle beam dwell so as to irradiate the particle beam onto a target, comprising:
   a first deflector having a maximum deflection amount which enables the first deflector to move the particle beam along the first axis to a maximum width of the target;
   a second deflector having a maximum deflection amount which enables the second deflector to move the particle beam along the first axis, the maximum deflection amount by the second deflector being less than the maximum deflection amount by the first deflector; and
   a scanning control apparatus which controls the first deflector and the second deflector,
   wherein the scanning control apparatus is configured to (i) perform a control in which the particle beam is moved by increasing at least a deflection amount by the second deflector when the particle beam is moved, and (ii) subsequently perform a deflection substitution control in which a deflection by the second deflector is substituted by a deflection by the first deflector by decreasing the deflection amount by the second deflector and changing a deflection amount by the first deflector so as to make a position of the particle beam in the target dwell.

2. The particle irradiation system according to claim 1, wherein the scanning control apparatus is configured to control a rate of change of deflection amount by the second deflector, which increases the deflection amount when the particle beam moves, to be faster than a rate of change of deflection amount by the first deflector which changes the deflection amount when the particle beam dwells.

3. The particle irradiation system according to claim 1, wherein the first deflector deflects the particle beam by an electromagnet.

4. The particle irradiation system according to claim 3, wherein the second deflector deflects the particle beam by an electromagnet.

5. The particle irradiation system according to claim 2, wherein the second deflector deflects the particle beam by an electric field.

6. The particle irradiation system according to claim 1, further comprising:
   a beam position monitor which obtains an information of a position of the particle beam which is scanned, wherein a feedback control is added to the control, in which the deflection amount by the second deflector is decreased, by the information from the beam position monitor when the particle beam dwells.

7. The particle irradiation system according to claim 4, wherein the first deflector comprises an excitation coil of an electromagnet and a first power source which supplies a current to the excitation coil and the second deflector comprises the excitation coil of the electromagnet and a second power source which supplies a current to the excitation coil.

8. The particle irradiation system according to claim 4, wherein
- an electromagnet comprises a first excitation coil and a second excitation coil on the same iron core;
- the first deflector comprises the first excitation coil and a first power source which supplies a current to the first excitation coil; and
- the second deflector comprises the second excitation coil and a second power source which supplies a current to the second excitation coil.

9. The particle irradiation system according to claim 3, wherein the second deflector is disposed at a position which is a particle beam incident side of a deflection electromagnet which deflects a main direction of particle beam traveling so as to guide the particle beam to the target.

10. The particle irradiation system according to claim 3, wherein (i) the system has the configuration of a rotating gantry and (ii) the second deflector is disposed at a particle beam incident side of a deflection electromagnet which is disposed at a most downstream side of a particle beam traveling the rotating gantry.

11. A particle beam irradiation method in which a target is irradiated by repeating an operation of moving the particle beam along a first axis and making the particle beam dwell so as to scan by a first deflector having a maximum deflection amount which enables the first deflector to move an incident particle beam along the first axis to a maximum width of the target and a second deflector having a maximum deflection amount, which enables the second deflector to move the particle beam along the first axis, and is less than the maximum deflection amount by the first deflector, the method comprising:

- increasing at least a deflection amount by the second deflector so as to move the particle beam in the target when the particle beam moves; and
- once the particle beam is moved within the target, decreasing the deflection amount by the second deflector; and
- changing a deflection amount by the first deflector in such a manner that a deflection by the second deflector is gradually substituted by a deflection by the first deflector so as to make a position of the particle beam in the target dwell.

12. The particle beam irradiation method according to claim 11, wherein a rate of change of deflection amount by the second deflector, which increases the deflection amount when a particle beam moves, is faster than a rate of change of deflection by the first deflector, which changes the deflection amount when the particle beam dwells.

* * * * *